(12) United States Patent
Zhu et al.

(10) Patent No.: US 7,074,804 B2
(45) Date of Patent: Jul. 11, 2006

(54) CCI-779 ISOMER C

(75) Inventors: Tianmin Zhu, Monroe, NY (US); James F. Mattes, Doylestown, PA (US)

(73) Assignee: Wyeth, Madison, NJ (US)

( * ) Notice: Subject to any disclaimer, the term of this patent is extended or adjusted under 35 U.S.C. 154(b) by 185 days.

(21) Appl. No.: 10/889,247

(22) Filed: Jul. 12, 2004

(65) Prior Publication Data

US 2005/0014777 A1 Jan. 20, 2005

Related U.S. Application Data

(60) Provisional application No. 60/487,712, filed on Jul. 16, 2003.

(51) Int. Cl.
*C07D 498/18* (2006.01)
*A61K 31/435* (2006.01)

(52) U.S. Cl. .................................. 514/291; 540/456
(58) Field of Classification Search ................ 540/456; 514/291
See application file for complete search history.

(56) References Cited

U.S. PATENT DOCUMENTS

| 5,362,718 | A | 11/1994 | Skotnicki et al. |
| 5,661,156 | A | 8/1997 | Holt et al. |
| 6,277,983 | B1 | 8/2001 | Shaw et al. |

FOREIGN PATENT DOCUMENTS

| WO | WO-95/28406 A | 10/1995 |
| WO | WO-02/26746 A | 4/2002 |
| WO | WO-02/28866 A | 4/2002 |

OTHER PUBLICATIONS

Steffan et al, Base Catalyzed Degradations of Rapamycin, Tetrahedron Letters, vol. 34, No. 23, pp. 3699-2702, (1993).
Skotnicki et al, Synthesis of Secorapamycin Esters and Amides[1], Tetrahedron Letters, vol. 35, No. 2, pp. 197-200, (1994).
Sehgal, Sirolimus: A New Immunosuppressive Agent, Chapter 12.1, Principles of Drug Development in Transplantation and Autoimmunity, pp. 271-282, (1996).
Caufield et al, Structure-Activity Involving Modifications to the Macrolides FK-506 and Rapamycin, Current Pharmaceutical Design, vol. 1, No. 2, pp. 145-160, (1995).
Sehgal et al, Rapamycin: A Novel Immunosuppressive Macrolide, Medicinal Research Reviews, vol. 14, No. 1, pp. 1-22, (Jan. 1994).
Hughes et al, The Isolation, Synthesis and Characterization of An Isomeric Form of Rapamycin, Tetrahedron Letters, vol. 33, No. 33, pp. 4739-4742, (1992).

*Primary Examiner*—Bruck Kifle
(74) *Attorney, Agent, or Firm*—Howson & Howson; Arnold S. Milowsky

(57) ABSTRACT

Purified CCI-779 Isomer C is provided, as are pharmaceutical compositions and kits containing same.

28 Claims, No Drawings

CCI-779 ISOMER C

CROSS-REFERENCE TO RELATED APPLICATION

This application the benefit under 35 USC 119(e) of the priority of U.S. patent application No. 60/487,712, filed Jul. 16, 2003.

BACKGROUND OF THE INVENTION

This invention relates to the preparation and use of a purified form of Isomer C of rapamycin 42-ester with 3-hydroxy-2-(hydroxymethyl)-2-methylpropionic acid (CCI-779).

Rapamycin 42-ester with 3-hydroxy-2-(hydroxymethyl)-2-methylpropionic acid (CCI-779) is an ester of rapamycin which has demonstrated significant inhibitory effects on tumor growth in both in vitro and in vivo models.

CCI-779 may delay the time to progression of tumors or time to tumor recurrence which is more typical of cytostatic rather than cytotoxic agents. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of CCI-779 that results in the G1-S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the G1 phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

The preparation and use of hydroxyesters of rapamycin, including CCI-779, are disclosed in U.S. Pat. Nos. 5,362,718 and 6,277,983, which are hereby incorporated by reference.

SUMMARY OF THE INVENTION

We have now found that when prepared and isolated according the above patents, CCI-779 exists as a mixture containing about 95 wt % of Isomer B and 30 wt % isomer C (as measured by high performance liquid chromatograph (HPLC)). The structures of each are provided below.

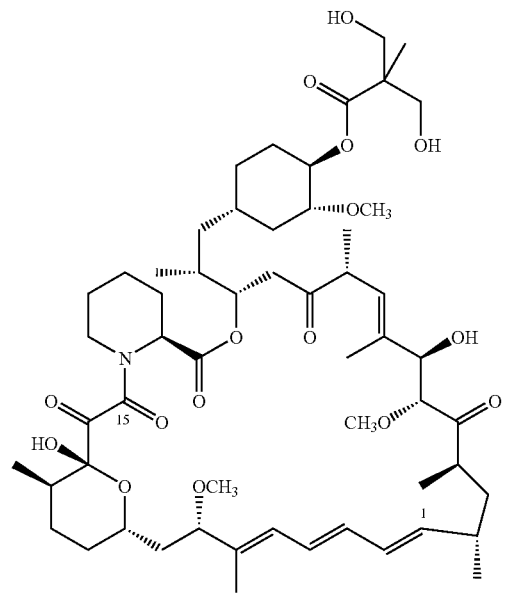

CCI-779 Isomer B

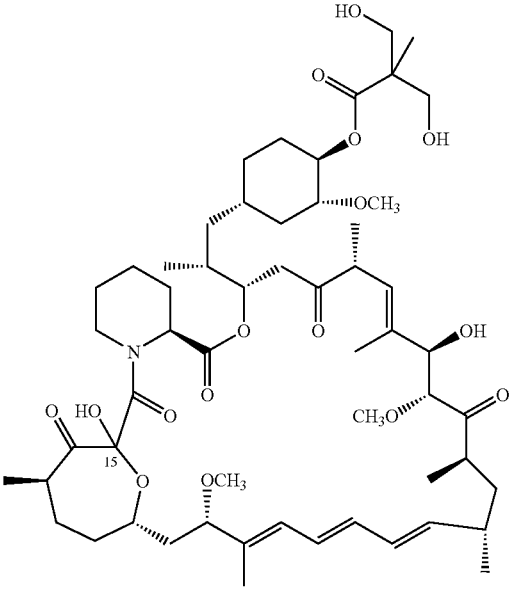

CCI-779 Isomer C

When formulated in solid form CCI-779 Isomer C is stable under storage conditions for extended periods of time. CCI-779 Isomer C is also stable when in an aqueous suspension.

Other aspects and advantages of the present invention will be readily apparent from the followed detailed description of the invention.

DETAILED DESCRIPTION OF THE INVENTION

This invention provides the preparation and use of purified CCI-779 Isomer C; this isomer is also referred to as the oxepane isomer of CCI-779. Accordingly, this invention provides CCI-779 Isomer C substantially free of CCI-779 Isomer B.

As used herein, the term "CCI-779" when used without any reference to isomers means rapamycin 42-ester with 3-hydroxy-2-(hydroxymethyl)-2-methylpropionic acid containing about 95 wt % of CCI-779 Isomer B and 3 wt % CCI-779 Isomer C.

As used herein, the term "purified" means having a purity of greater than 50 wt % of Isomer C. It is preferred that the purified CCI-779 Isomer C has a purity of greater than 75 wt %, more preferred that the CCI-779 Isomer C has a purity of greater than 90 wt %, and most preferred that the CCI-779 Isomer C has a purity of greater than 95 wt %, from Isomer B. Such purity can be readily measured by HPLC.

As used herein, the term "substantially free of" means CCI-779 Isomer C as a compound, composition, or mixture which contains less than 10 wt % CCI-779 Isomer B, and preferably less than 5 wt % CCI-779 Isomer B, more preferably less than 2 wt % CCI-779-isomer B. The percent of Isomer C to Isomer B can readily be determined by HPLC.

As used in accordance with this invention, the term "treatment" means alleviating the symptoms in a mammal having a disease or disorder by providing said mammal with an effective amount of CCI-779 Isomer C.

As used in accordance with this invention, the term "providing," with respect to providing CCI-779 Isomer C means either directly administering CCI-779 Isomer C, or administering a prodrug, derivative, or analog which will form an effective amount of CCI-779 Isomer C within the body.

The preparation of CCI-779 is described in U.S. Pat. No. 5,362,718, which is hereby incorporated by reference. A regiospecific synthesis of CCI-779 is described in U.S. Pat. No. 6,277,983, which is hereby incorporated by reference. When prepared according to the above patents, CCI-779 exists as an equilibrium mixture containing about 95 wt % of Isomer B and 3 wt % isomer C (as measured by HPLC).

CCI-779 Isomer C exists in equilibrium with CCI-779 Isomer B, according to the following scheme. Under conditions described herein, the equilibrium can be driven from the greatly favored Isomer B state to the Isomer C state followed by isolation and purification of CCI-779 Isomer C.

The conversion of CCI-779 Isomer B to CCI-779 Isomer C can be accomplished in a mixture of aqueous buffer and organic solvent in the range of pH 4 to pH 10. More particularly, the method of the invention involves dissolving CCI-779 in a solution containing an organic solvent and an aqueous solvent, where the aqueous solvent has a pH of from 4 to 10, 5 to 9, 6 to 9, or 7 to 9. The pH is preferred in the range of 8 and 9. Most preferred pH is about 8.5.

Any suitable aqueous buffer including, without limitation, phosphate buffered saline, triethylammonium acetate, and water with sodium citrate buffer, can be readily selected by one of skill in the art. It is preferred that the organic solvent is a polar aprotic solvent, i.e., a solvent that is polar but has no ability to be an H-bond donor. Examples of suitable polar aprotic solvents include dimethylsulfoxide (DMSO; $CH_3$—SO—$CH_3$), dimethylformamide, acetonitrile (H—CO—N$(CH_3)_2$), aldehydes (R—CHO), ketones (R—CO—R'), In one example below, the aqueous buffer is triethylammonium acetate (TEAA) and the polar aprotic solvent is acetonitrile. These are provided at a ratio of about 1:1, by volume. However, other suitable ratios of this buffer and solvent combination will be readily apparent to one of skill in the art. Similarly, other suitable aqueous buffers and organic solvents useful in the method of the invention will be readily apparent to those of skill in the art in view of this specification.

This conversion reaction can be performed at room temperature, i.e., about 22° C. to about 28° C. Alternatively, the conversion may be performed at lower or higher temperatures, as needed. Typically, conversion is allowed to proceed for about 30 to 45 minutes (or longer, as needed or desired) and is stopped by extraction of CCI-779 isomer C with a suitable organic solvent.

In one embodiment, the organic solvent used in the extraction is an aprotic solvent, i.e., a solvent whose molecules have a zero molecular dipole and whose hydrogen atoms are not bonded to an oxygen or nitrogen. Examples include the hydrocarbons (e.g., alkanes, alkenes, and alkynes). In the examples below, the non-polar aprotic solvent is methylene chloride. Other suitable aprotic solvents will be readily apparent to one of skill in the art in view of the teachings herein.

Isolation of purified CCI-779 Isomer C can be accomplished using preparative chromatography techniques, such as are well known to those of skill in the art. See, generally, PREPARATIVE CHROMATOGRAPHY, by R. P. W. Scott, Chrom-Ed Book Series, available on-line and Guiochon, G. et al, FUNDAMENTALS OF PREPARATIVE AND NON-LINEAR CHROMATOGRAPHY, $1^{st}$ Ed. Academic Press (1994).

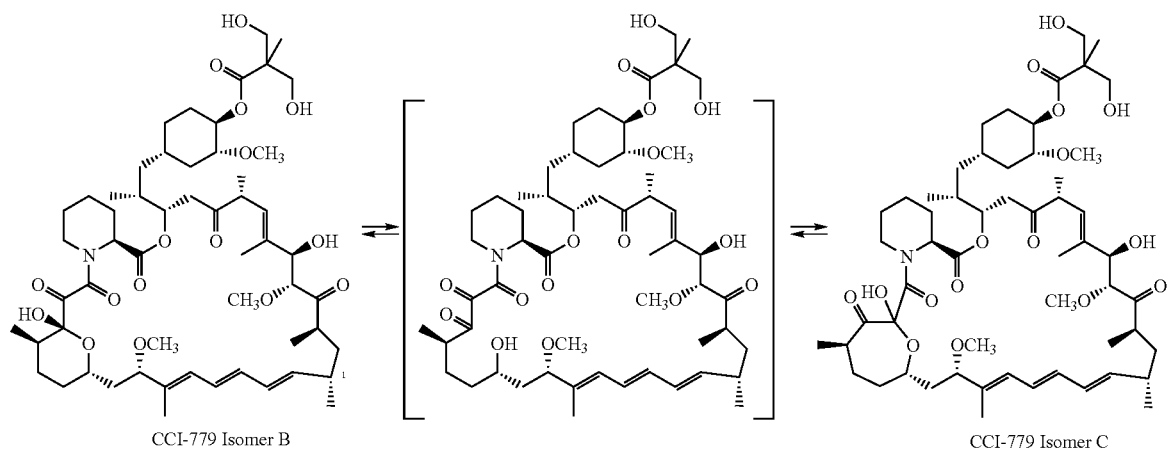

CCI-779 Isomer B ⇌ [ ] ⇌ CCI-779 Isomer C

Antifungal activity for CCI-779 Isomer C was established by evaluating it against several strains of fungi. Briefly the following procedure was used to evaluate such activity. A 96 well microtiter plate was filled (50 µL/well) with RPMI 1640. The compounds to be evaluated were placed in appropriate wells and serial diluted in successive wells to provide several dilutions. The concentration ranged from 64 to 0.06 mg/mL. An adjusted inoculum of fungi (50 µL) was added to each well and plates were incubated at 35° C. for 24–48 h. The MIC is the lowest concentration of compound which completely inhibited growth of organism in the wells. The following table shows the results obtained in this standard pharmacological test procedure. Where the same fungi name is listed more than once, it indicates that more than one strain was evaluated.

TABLE 1

ANTIFUNGAL ACTIVITY (MIC in µg/mL)

| Yeast/ Fungi | ID | CCI-779 Isomer C | Ny-statin | Amphotericin B |
|---|---|---|---|---|
| Candida albicans | 1063 | 4 | 1 | ≦0.06 |
| Candida albicans | 1117 | 4 | 1 | 0.12 |
| Candida albicans | ATCC 90028 | 4 | 1 | 0.12 |
| Candida parapsilosis | 94-9 | 4 | 1 | 0.12 |
| Candida parapsilosis | 94-8 | 4 | 2 | ≦0.06 |
| Candida parapsilosis | ATCC 90018 | 4 | 2 | ≦0.06 |
| Candida pseudotropicalis | ATCC 28838 | 4 | 1 | ≦0.06 |
| Candida tropicalis | 94-14 | 4 | 1 | ≦0.06 |
| Candida tropicalis | 94-13 | 4 | 1 | ≦0.06 |
| Candida krussii | 94-2 | 4 | 1 | 0.12 |
| Candida lusitaniae | 94-3 | 8 | 1 | ≦0.06 |
| Candida rugosa | 94-10 | 16 | 1 | 0.25 |
| Aspergillus fumigatus | ATCC 26933 | >32 | 2 | 0.25 |
| Aspergillus niger | S430 | 32 | 1 | 0.25 |
| Aspergillus niger | S399 | 32 | 2 | 0.50 |

The results obtained in this standard pharmacological test procedure demonstrate that the CCI-779 Isomer C is useful as an antifungal agent. CCI-779 Isomer C is also useful as an antineoplastic agent; in particular, it is useful against solid tumors, including sarcomas and carcinomas; and more particularly against astrocytomas, prostate cancer, breast cancer, colon cancer, small cell lung cancer, and ovarian cancer; and adult T-cell leukemia/lymphoma. CCI-779 Isomer C is also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemia/lymphoma; fungal infections; hyperproliferative vascular diseases such as restenosis; graft vascular atherosclerosis; and cardiovascular disease, cerebral vascular disease, and peripheral vascular disease, such as coronary artery disease, cereberovascular disease, arteriosclerosis, atherosclerosis, nonatheromatous arteriosclerosis, or vascular wall damage from cellular events leading toward immune mediated vascular damage, and inhibiting stroke or multi-infarct dementia.

When used for restenosis, it is preferred that CCI-779 Isomer C is used to treat restenosis that occurs following an angioplasty procedure. When used for this treating restenosis following an angioplasty, CCI-779 Isomer C can be administered prior to the procedure, during the procedure, subsequent to the procedure, or any combination of the above.

Dosage regimens are expected to vary according to the route of administration. For example, dosages for oral administration are often up to five to tenfold greater than for i.v. administration. For example, in one embodiment, an oral dosage of CCI-779 will in the range of about 2 to about 100 mg/day, 5 mg/day to 75 mg/day, 10 mg/day to 50 mg/day, 15 mg/day to 35 mg/day, or about 20 mg/day to 25 mg/day for an adult. However, this dosage can be adjusted upwardly or downwardly by one of skill in the art, depending upon the indication being treated, the size of the patient, and other factors which are known those of skill in the art.

Suitable oral formulations for CCI-779 isomer C can be prepared as described for CCI-779, as described in WO 2004/026280 and U.S. patent application Ser. No. 10/663,506, which is hereby incorporated by reference. Such an oral formulation contains a granulation prepared using a wet granulation process. The granulation contains CCI-779 isomer C, a water soluble polymer, a pH modifying agent, a surfactant, and an antioxidant. In one embodiment, the formulation contains from 0.1 to 30 wt %, from 0.5 to 25 wt %, from 1 to 20 wt %, from 5 to 15 wt %, or from 7 to 12 wt % (wt/wt) CCI-779 isomer C, from 0.5 to 50 wt %, from 1 to 40 wt %, from 5 to 35 wt %, from 10 to 25 wt %, or from 15 to 20 wt % (wt/wt) water soluble polymer, from 0.5 to 10 wt %, 1 to 8 wt %, or 3 to 5 wt % (wt/wt) surfactant, and from 0.001 wt % to 1 wt %, 0.01 wt % to 1 wt %, or 0.1 wt % to 0.5 wt % (wt/wt) antioxidant. However, other embodiments may contain more, or less, of these components.

The oral formulation may also contain suitable chelating agents, fillers, binders, surfactants, and the like to facilitate the granulation and tableting process. It is preferred that the wet granulation be performed with a hydroalcoholic solvent system comprising water and an alcohol, with ethanol being the preferred alcoholic component.

Typical water soluble polymers include, but are not limited to, polyvinylpyrrolidone (PVP), hydroxypropylmethylcellulose (HPMC), polyethylene glycol (PEG), and cyclodextrin or mixtures thereof. It is preferred that the water-soluble polymer is PVP, and having a molecular weight of between 2.5 and 60 kilodaltons. Any given oral formulation useful in the invention may contain multiple ingredients of each class of component. For example, an oral formulation containing an antioxidant may contain one or more antioxidants as the antioxidant component.

Acceptable pH modifying agents include, but are not limited to citric acid, sodium citrate, dilute HCl, and other mild acids or bases capable of buffering a solution containing CCI-779 isomer C to a pH in the range of about 4 to about 6. Acceptable antioxidants include, but are not limited to, citric acid, d,l-α-tocopherol, BHA, BHT, monothioglycerol, ascorbic acid, and propyl gallate. It is expected that the antioxidants of the oral formulations used in this invention will be used in concentrations ranging from 0.001 wt % to 3 wt % wt/wt. Chelating agents, and other materials capable of binding metal ions, such as ethylene diamine tetra acetic acid (EDTA) and its salts are capable of enhancing the stability of CCI-779 isomer C. Surfactants may include polysorbate 80, sodium lauryl sulfate, sodium dodecyl sulfate, salts of bile acids (taurocholate, glycocholate, cholate, deoxycholate, etc.) that may be combined with lecithin. Alternatively, ethoxylated vegetable oils, such as Cremophor EL, vitamin E tocopherol propylene glycol succinate (Vitamin E TGPS), polyoxyethylene-polyoxypropylene block copolymers, and poloxamers. Binders, fillers, and disintegrants such as sucrose, lactose, microcrystalline cellulose, croscarmellose sodium, magnesium stearate, gum acacia, cholesterol, tragacanth, stearic acid, gelatin, casein, lecithin (phosphatides), carboxymethylcellulose calcium, carboxymethylcellulose sodium, methylcellulose, hydroxyethylcellulose, hydroxypropylcellulose, hydroxypropylmethylcellulose phthalate, noncrystalline cellulose, cetostearyl alcohol, cetyl alcohol, cetyl esters wax, dextrates, dextrin, lactose, dextrose, glyceryl monooleate, glyceryl monostearate, glyceryl palmitostearate, polyoxyethylene alkyl ethers, polyethylene glycols, polyoxyethylene castor oil derivatives, polyoxyethylene stearates, and polyvinyl alcohol, and the like may also be incorporated into the oral formulation.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Particularly suitable injectable formulations for CCI-779 isomer C can prepared in a manner similar to those described for CCI-779 in WO 2004/011000 and U.S. patent application Ser. No. 10/626,943, which is hereby incorporated by reference. In this embodiment, the injectable formulation useful in the invention provides a CCI-779 isomer C cosolvent concentrate containing an parenterally acceptable solvent and an antioxidant as described above and a parenteral formulation containing CCI-779 isomer C, composed of CCI-779 isomer C, an parenterally acceptable cosolvent, an antioxidant, a diluent solvent, and a surfactant. Any given formulation useful in this invention may contain multiple ingredients of each class of component. For example, a parenterally acceptable solvent can include a non-alcoholic solvent, an alcoholic solvent, or mixtures thereof. Examples of suitable non-alcoholic solvents include, e.g., dimethylacetamide, dimethylsulfoxide or acetonitrile, or mixtures thereof. "An alcoholic solvent," may contain one or more alcohols as the alcoholic solvent component of the formulation. Examples of solvents useful in the formulations invention include, without limitation, ethanol, propylene glycol, polyethylene glycol 300, polyethylene glycol 400, polyethylene glycol 600, polyethylene glycol 1000, or mixtures thereof. These cosolvents are particularly desirable because degradation via oxidation and lactone cleavage occurs to a lower extent for these cosolvents. Further, ethanol and propylene glycol can be combined to produce a less flammable product, but larger amounts of ethanol in the mixture generally result in better chemical stability. A concentration of 30 to 100% v/v of ethanol in the mixture is preferred.

In this embodiment, the stability of CCI-779 isomer C in parenterally acceptable alcoholic cosolvents is enhanced by addition of an antioxidant to the formulation. Acceptable antioxidants include, but are not limited to, citric acid, d,l-α-tocopherol, BHA, BHT, monothioglycerol, ascorbic acid, propyl gallate, and mixtures thereof. Generally, the parenteral formulations useful in this embodiment of the invention will contain an antioxidant component(s) in a concentration ranging from 0.001% to 1% w/v, or 0.01% to 0.5% w/v, of the cosolvent concentrate, although lower or higher concentrations may be desired. Of the antioxidants, d,l-α-tocopherol is particularly desirable and is used at a concentration of 0.01 to 0.1% w/v with a preferred concentration of 0.075% w/v of the cosolvent concentrate.

In certain embodiments, the antioxidant component of the formulation of the invention also exhibits chelating activity. Examples of such chelating agents include, e.g., citric acid, acetic acid, and ascorbic acid (which may function as both a classic antioxidant and a chelating agent in the present formulations). Other chelating agents include such materials as are capable of binding metal ions in solution, such as ethylene diamine tetra acetic acid (EDTA), its salts, or amino acids such as glycine are capable of enhancing the stability of CCI-779 isomer C. In some embodiments, components with chelating activity are included in the formulations of the invention as the sole "antioxidant component". Typically, such metal-binding components, when acting as chelating agents are used in the lower end of the range of concentrations for the antioxidant component provided herein. In one example, citric acid enhanced the stability of CCI-779 isomer C when used at a concentration of less than 0.01% w/v. Higher concentrations are less stable solutions and thus, less desirable for products to be subject to long-term storage in liquid form. Additionally, such chelating agents may be used in combination with other antioxidants as part of the antioxidant component of the invention. For example, an acceptable formulation may contain both citric acid and d,l-α-tocopherol. Optimal concentrations for the selected antioxidant(s) can be readily determined by one of skill in the art, based upon the information provided herein.

Advantageously, in certain embodiments of the parenteral formulations useful in the invention, precipitation of CCI-779 isomer C upon dilution with aqueous infusion solutions or blood is prevented through the use of a surfactant contained in the diluent solution. The most important component of the diluent is a parenterally acceptable surfactant. One particularly desirable surfactant is polysorbate 20 or polysorbate 80. However, one of skill in the art may readily select other suitable surfactants from among salts of bile acids (taurocholate, glycocholate, cholate, deoxycholate, etc.) which are optionally combined with lecithin. Alternatively, ethoxylated vegetable oils, such as a pegylated castor oil [e.g., such as PEG-35 castor oil which is sold, e.g., under the name Cremophor EL, BASF], vitamin E tocopherol propylene glycol succinate (Vitamin E TGPS), and polyoxyethylene-polyoxypropylene block copolymers can be used in the diluent as a surfactant, as well as other members of the polysorbate family such as polysorbate 20 or 60 Other components of the diluent may include water, ethanol, polyethylene glycol 300, polyethylene 400, polyethylene 600, polyethylene 1000, or blends containing one or more of these polyethylene glycols, propylene glycol and other parenterally acceptable cosolvents or agents to adjust solution osmolarity such as sodium chloride, lactose, mannitol or other parenterally acceptable sugars, polyols and electrolytes. It is expected that the surfactant will comprise 2 to 100% w/v of the diluent solution, 5 to 80% w/v, 10 to 75% w/v, 15 to 60% w/v, and preferably, at least 5% w/v, or at least 10% w/v, of the diluent solution.

A parenteral formulation useful in the invention can be prepared as a single solution, or preferably can be prepared as a cosolvent concentrate containing CCI-779 isomer C, an alcoholic solvent, and an antioxidant, which is subsequently combined with a diluent that contains a diluent solvent and suitable surfactant. Prior to use, the cosolvent concentrate is mixed with a diluent comprising a diluent solvent, and a surfactant. When CCI-779 isomer C is prepared as a cosolvent concentrate according to this invention, the concentrate can contain concentrations of CCI-779 isomer C from 0.05 mg/mL, from 2.5 mg/mL, from 5 mg/mL, from 10 mg/mL or from 25 mg/mL up to approximately 50 mg/ml. The concentrate can be mixed with the diluent up to approximately 1 part concentrate to 1 part diluent, to give parenteral formulations having concentrations of CCI-779 isomer C from 1 mg/mL, from 5 mg/mL, from 10 mg/mL, from 20 mg/mL, up to approximately 25 mg/ml. For example the concentration of CCI-779 isomer C in the parenteral formulation may be from about 2.5 to 10 mg/mL. This invention also covers the use of formulations having lesser concentrations of CCI-779 isomer C in the cosolvent concentrate, and formulations in which one part of the concentrate is mixed with greater than 1 part of the diluent, e.g., concentrate: diluent in a ratio of about 1:1.5, 1:2, 1:3, 1:4, 1:5, or 1:9 v/v and so on, to CCI-779 isomer C parenteral formulations having a CCI-779 isomer C concentration down to the lowest levels of detection.

Typically the antioxidant may comprise from about 0.0005 to 0.5% w/v of the formulation. The surfactant may for example comprise from about 0.5% to about 10% w/v of the formulation. The alcoholic solvent may for example comprise from about 10% to about 90% w/v of the formulation.

The parenteral formulations useful in this invention can be used to produce a dosage form that is suitable for administration by either direct injection or by addition to sterile infusion fluids for intravenous infusion.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The purified CCI-779 isomer C of the invention may be formulated for any suitable delivery route and vehicle and assembled in the form of a kit of parts. The invention therefore includes a product containing (a) CCI-779 isomer C for use in treating a mammal. The invention also includes a pharmaceutical pack containing a course of treatment of a neoplasm for one individual mammal, wherein the pack contains (a) units of CCI-779 isomer C in unit dosage form.

Thus, the CCI-779 Isomer C of the invention can be formulated as a pharmaceutical composition and, optionally, assembled in the form of a kit, for use in treatment of a mammal. Such a composition or kit can be used as an antineoplastic agent, and in particular, in treatment of solid tumors, including sarcomas and carcinomas; and more particularly against astrocytomas, prostate cancer, breast cancer, colon cancer, small cell lung cancer, and ovarian cancer; and adult T-cell leukemia/lymphoma. CCI-779 Isomer C-containing compositions and kits are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemia/lymphoma; fungal infections; hyperproliferative vascular diseases such as restenosis; graft vascular atherosclerosis; and cardiovascular disease, cerebral vascular disease, and peripheral vascular disease, such as coronary artery disease, cereberovascular disease, arteriosclerosis, atherosclerosis, nonatheromatous arteriosclerosis, or vascular wall damage from cellular events leading toward immune mediated vascular damage, and inhibiting stroke or multiinfarct dementia.

The following procedures describe one method for the preparation and characterization of CCI-779 Isomer C. This example is illustrative only, and does not limit the invention.

CCI-779 (300 mg 0.29 mmol) was dissolved in about 50 wt % 0.2 M TEAA buffer pH 8.5 and 50 wt % acetonitrile. The solution was kept at room temperature for about 45 min. The conversion was stopped by $CH_2Cl_2$ extraction. The organic layer was reduced by rotary evaporation system to dryness. The isolation of isomer C was performed by preparative NOVPAK™ HR C-18 column (300×19 mm) using the mobile phase consisted of 38 wt % A, 62 wt % B. A is 90 wt % 0.02 M TEAA buffer pH 3.5 10 wt % acetonitrile. B is 10 wt % 0.02 M TEM buffer pH 3.5 with 90 wt % acetonitrile. The flow rate was 20 mL/min. The fraction of isomer C (20 min) was collected and extracted with $CH_2Cl_2$ using a separatory funnel. The organic layer was combined and washed with 2×50 mL water then the organic layer was dried with anhydrous $Na_2SO_4$. The organic solvent was reduced by rotary evaporation to about 1 mL. The product was transferred into a vial and precipitated by adding n-hexane. A second purification by preparative chromatography was usually necessary to obtain pure CCI-779 Isomer C. The white powder was obtained by using $N_2$ to blow away the solvent and the vial was put into speed-vac to dry overnight. The purity of the isomer C for each purification step was analyzed by analytical HPLC. (An Ultracarb™ ODS 150×4.6 mm, 5 μm in particle size from Phenomenex was used.) The mobile phase consisted of 60 wt % acetonitrile, 40 wt % water with 0.02 M sodium citrate buffer at pH 4.2. The column temperature was at 45° C. and flow rate was at 1.5 mL/min. The detection wavelength was set at 280 nm. The injection volume was 10 μl). The retention time is 15 min. for CCI-779 isomer B and 17 min. for CCI-779 isomer C.) Based on AUC analysis of the HPLC, CCI-779 Isomer C was produced in 98.4 wt % purity, and contained 1.6 wt % CCI-779 Isomer B. ESI mass spectrometry indicates molecular ion $[M+NH_4]^+$ m/e 1047.6 which is same as the reference sample of CCI-779.

$^1$H NMR data were acquired on both 400 and 600 MHz Varian Unity Plus™ spectrometers with a probe temperature of 25° C. The sample was prepared in acetone-d6 and compared to a solution of CCI-779 which was also prepared in acetone-d6. Resonances that differentiate a seven membered ring hemiketal (CCI-779 Isomer C) structure from the six membered ring hemiketal (CCI-779 Isomer B) structure include the following:

(1) In the proton spectrum for CCI-779 Isomer C, C-12αCH$_3$ is observed at 1.17 ppm for both rotational isomers. This equivalence is deduced from the chemical shift differences correlating the C-12αCH$_3$ resonances in the COSY spectrum to two distinct H-11 rotomer resonances at 1.22 and 1.25 ppm, and to H-12 resonances at 3.18 and 3.24 ppm which are further discussed below. This differs from the major, 80 wt % rotomer resonance of C-12αCH$_3$ observed at 0.92 ppm in the CCI-779 reference spectrum.

(2) H-12 rotomer resonances are observed at 3.18 and 3.24 ppm in Isomer C. These shifts are consistent with the structure of the H-12 methine proton to a ketone carbonyl in CCI-779 Isomer C from the major rotomer resonance of CCI-779 observed at 2.21 ppm for H-12 methine proton to a hemiketal.

(3) Indirect detection shows three distinct pairs of rotomeric ketone carbonyl resonances correlated to various proton resonances in the HMBC spectrum. All three ketone carbonyls are downfield of 200 ppm in this spectrum. Using the HMBC data to assign these ketone resonances to CCI-779 Isomer C, the C-27 carbonyl is at 210 ppm, C-33 is at 213 ppm and C-14 is at 211 ppm.

Two deuterium exchangeable singlet rotomeric resonances for the C-15αOH are observed in the proton spectrum at 5.9 and 6.1 ppm and correlate in the HMBC spectrum to the C-14 ketone carbon resonances at 211 ppm, to the C-16 amide carbon resonances at 169 ppm, and to the C-15 hemiketal carbon resonances at 99 ppm. This triad of two and three bond OH couplings to non-protonated carbons is only consistent with structure for CCI-779 Isomer C.

In the proton spectrum for the reference sample, CCI-779 a deuterium exchangeable singlet resonance at 5.25 ppm correlates in the HMBC spectrum to the C-15 ketone carbon at 198 ppm and to the C-14 hemiketal carbon at 100 ppm. No correlation to the C-16 amide carbon at 168 ppm is observed. This data is consistent with the CCI-779 structure.

All patents, patent applications, articles, and other documents referenced herein are incorporated by reference. It will be clear to one of skill in the art that modifications can be made to the specific embodiments described herein without departing from the scope of the invention.

The invention claimed is:

1. CCI-779 Isomer C having a purity of greater than 50 wt %.

2. The CCI-779 Isomer C according to claim 1, wherein the purity of CCI-779 Isomer C is greater than 75 wt %.

3. The CCI-779 Isomer C according to claim 1, wherein the purity of CCI-779 Isomer C is greater than 90 wt %.

4. The CCI-779 Isomer C according to claim 1, wherein the purity of CCI-779 Isomer C is greater than 95 wt %.

5. CCI-779 Isomer C substantially free of CCI-779 Isomer B.

6. The CCI-779 Isomer C according to claim 5, which contains less than 5 wt % CCI-779 Isomer B.

7. The CCI-779 Isomer C according to claim 5, which contains less than 2 wt % CCI-779 Isomer B.

8. CCI-779 Isomer C prepared from CCI-779 by
a) dissolving CCI-779 in a solution containing an organic solvent and an aqueous solvent, said aqueous solvent having a pH in the range of 4 to 10;
b) extracting the CCI-779 Isomer C into an organic solvent.

9. The CCI-779 Isomer C prepared according to claim 8, wherein the organic solvent in step a) is a polar aprotic solvent.

10. The CCI-779 Isomer C prepared according to claim 9, wherein the organic solvent in step a) is acetonitrile.

11. The CCI-779 Isomer C prepared according to claim 8, wherein the pH is in the range of 7 to 9.

12. The CCI-779 Isomer C prepared according to claim 11, wherein the pH is in the range of 7.5 to 8.5.

13. The CCI-779 Isomer C prepared according to claim 8, wherein the organic solvent of step b) is an aprotic solvent.

14. The CCI-779 Isomer C prepared according to claim 13, wherein the aprotic solvent of step b) is methylene chloride.

15. A process for preparing purified CCI-779 Isomer C which comprises, a) dissolving CCI-779 in a solution containing an organic solvent and an aqueous solvent, said aqueous solvent having a pH in the range of 4 and 10;

b) extracting the CCI-779 Isomer C into an organic solvent.

16. The process according to claim 15, wherein the organic solvent in step a) is a polar aprotic solvent.

17. The process according to claim 16, wherein the organic solvent in step a) is acetonitrile.

18. The process according to any claim 15, wherein the pH is in the range of 7 to 9.

19. The process according to claim 18, wherein the pH is in the range of 7.5 to 8.5.

20. The process according to claim 15, wherein the organic solvent of step b) is a non-polar aprotic solvent.

21. The process according to claim 20, wherein the organic solvent of step b) is a non-polar aprotic solvent.

22. The process according to claim 21, wherein the organic solvent of step b) is methylene chloride.

23. A pharmaceutical composition comprising purified CCI-779 isomer C according to claim 1 and a pharmaceutically acceptable carrier.

24. A pharmaceutical composition comprising purified CCI-779 isomer C according to claim 5 and a pharmaceutically acceptable carrier.

25. A pharmaceutical composition comprising purified CCI-779 isomer C according to claim 8 and a pharmaceutically acceptable carrier.

26. A pharmaceutical pack containing a course of treatment for a mammal, wherein the pack contains (a) units of purified CCI-779 isomer C according to claim 1 in unit dosage form.

27. A pharmaceutical pack containing a course of treatment for a mammal, wherein the pack contains (a) units of purified CCI-779 isomer C according to claim 5 in unit dosage form.

28. A pharmaceutical pack containing a course of treatment for a mammal, wherein the pack contains (a) units of purified CCI-779 isomer C according to claim 8 in unit dosage form.

* * * * *